United States Patent
McClellan et al.

(10) Patent No.: US 8,039,012 B2
(45) Date of Patent: Oct. 18, 2011

(54) TOPICAL COMPOSITIONS FOR ANTI-AGING AND METHODS OF USING SAME

(75) Inventors: Stephanie N. McClellan, Corona del Mar, CA (US); Ashton A. Kaidi, Anaheim Hills, CA (US)

(73) Assignee: McKA, LLC, Corona Del Mar, CA (US)

( * ) Notice: Subject to any disclaimer, the term of this patent is extended or adjusted under 35 U.S.C. 154(b) by 0 days.

(21) Appl. No.: 12/831,714

(22) Filed: Jul. 7, 2010

(65) Prior Publication Data

US 2010/0272832 A1  Oct. 28, 2010

Related U.S. Application Data

(62) Division of application No. 11/169,239, filed on Jun. 28, 2005, now Pat. No. 7,767,215.

(60) Provisional application No. 60/584,463, filed on Jun. 29, 2004.

(51) Int. Cl.
  *A61K 31/728*  (2006.01)
  *A61K 31/375*  (2006.01)
  *A61K 31/56*  (2006.01)
  *A61P 17/00*  (2006.01)

(52) U.S. Cl. .......... 424/401; 424/729; 514/169; 514/54; 514/171; 514/474

(58) Field of Classification Search .................. 424/401, 424/727, 729; 514/54, 171, 474, 169
See application file for complete search history.

(56) References Cited

U.S. PATENT DOCUMENTS

| | | | |
|---|---|---|---|
| 2,798,053 | A | 7/1957 | Brown |
| 5,262,407 | A | 11/1993 | Leveque et al. |
| 5,863,560 | A | 1/1999 | Osborne |
| 6,060,612 | A | 5/2000 | Hong et al. |
| 6,194,452 | B1 | 2/2001 | Murad |
| 6,238,678 | B1 | 5/2001 | Oblong et al. |
| 7,314,634 | B2 | 1/2008 | Hernandez et al. |

OTHER PUBLICATIONS

Bauza (2002) Date palm kernel extract exhibits antiaging properties and significantly reduces skin wrinkles. International Journal of Tissue Reactions. 24(4):131-136.
Creidi et al. (1994) Effect of a conjugated oestrogen (Premarin®) cream on ageing facial skin. A comparative study with a placebo cream. Maturitas 19:211-223.
(1986) McCutcheon's Detergents and Emulsifiers, North American Edition, pp. 317-324.
Pugliese (1994) Menopausal skin. Skin Inc. Mar./Apr.:69-77.
Richards et al. (1996) Human dermal fibroblast cells express prolactin In Vitro. J. Invest Dermatol 106:1250-1255.
Sagarin (1972) Cosmetics, Science and Technology. $2^{nd}$ Ed. vol. 1:32-43.
Sagarin (1972) Cosmetics, Science and Technology. $2^{nd}$ Ed. vol. 1:72-73.
Sagarin (1972) Cosmetics, Science and Technology. $2^{nd}$ Ed. vol. 2:443-465.
Schmidt (1996) Treatment of skin aging with topical estrogens. International Journal of Dermatology. 35(9):669-674.
Shiseido Co Ltd (1984) Database WPI Section Ch, Week 198412. Derwent Publications Ltd., Longon, GB; AN 1984-071324. XP002344031. JP 59 025311 A Abstract.
Edward Susman (2002) Dermatology—$20^{th}$ World Congress . IDrugs. 5(8):785-787.
http://web.archive.org/web/20000521072728/http://www.springboard4health.com/notebook/v_b3.html, (1999).

*Primary Examiner* — Sreeni Padmanabhan
*Assistant Examiner* — Sahar Javanmard
(74) *Attorney, Agent, or Firm* — Knobbe, Martens, Olson & Bear LLP

(57) ABSTRACT

A pharmaceutical composition for treatment of skin aging including a pharmaceutically effective amount of estriol; a pharmaceutically effective amount of estradiol; a pharmaceutically effective amount of hyaluronic acid; a pharmaceutically effective amount of green tea extract; and a pharmaceutically acceptable carrier is provided. In some embodiments, the composition further includes ascorbic acid, date palm extract, or a combination thereof. Also disclosed is a method for treating symptoms of skin aging and photoaging by administering a pharmaceutical composition having estriol, estradiol, hyaluronic acid, green tea extract, a pharmaceutically acceptable carrier and optionally, ascorbic acid and date palm extract. A method of promoting urogenital function is likewise provided wherein a pharmaceutical composition having estriol, estradiol, hyaluronic acid, and green tea extract is applied intravaginally.

8 Claims, 4 Drawing Sheets

TOPICAL COMPOSITIONS FOR ANTI-AGING AND METHODS OF USING SAME

RELATED APPLICATIONS

This application is a divisional of U.S. application Ser. No. 11/169,239, filed Jun. 28, 2005, which claims priority to U.S. Provisional Application Ser. No. 60/584,463, filed Jun. 29, 2004, all of which are herein incorporated by reference in their entireties.

BACKGROUND OF THE INVENTION

1. Field of the Invention

The disclosure relates to topical compositions for treating skin conditions associated with aging. More specifically, the invention includes compositions comprising estradiol, estriol, hyaluronic acid, green tea extract, and optionally ascorbic acid for topical administration to the skin. Also included within the scope of the invention are methods of ameliorating symptoms of skin aging including wrinkles, sun damage, rhytids, skin discoloration, rosacea, photoaging, hyperpigmentation, melasma, facial skin tightening including eyelids and jowls, and keratosis. Compositions and methods for improving the aesthetics of scars and promoting wound healing are similarly described. A composition and method for improving urogenital function is likewise provided.

2. Description of the Related Art

In the sixteenth century, Ponce de Leon searched the Americas in vain for the legendary fountain of youth. Nearly 500 years later, individuals still seek a magic youth potion to minimize the signs of aging. Cosmetic surgery to promote a youthful appearance has become a growth industry. Cosmetic treatments such as botox, collagen injections, chemical peels, and laser treatment have been embraced by many to reduce the signs of aging. In recent years, cosmeceuticals with potentially anti-aging effects are a booming business, due in part to the aging baby boomer population.

The human skin consists of two layers, the bottom thicker layer (dermis) and the top thinner layer (epidermis). Dermis is the layer which provides the strength, elasticity, and the thickness to the skin. The main cell type of the dermis is the fibroblast, which is responsible for synthesis and secretion of all the dermal matrix components such as collagen, elastin, and glycosaminoglycans. Collagen provides the strength, elastin is responsible for the elasticity, and glycosaminoglycans afford the skin moistness and plumpness.

With aging, the thickness of the dermal layer is reduced and this is believed to be partially responsible for the formation of wrinkles in aging skin. The top layer of human skin or the epidermis which provides the resilience and the barrier properties of the skin, is composed of many different cell types including keratinocytes, melanocytes, and Langerhans cells. Richards et al. reported that estrogen stimulates secretion of a protein, prolactin, by human dermal fibroblast cells and that prolactin then stimulates proliferation of keratinocytes. Richards et al., J. Invest. Dermatol. 106: 1250 (1996).

Estrogens and synthetic compounds which act like estrogens are known to increase the thickness of the dermal layer and to reduce wrinkle formation in the aging skin. The changes in the skin such as skin dryness, loss of skin elasticity and plumpness occurring after menopause, for example, are attributed to the lack of estrogen production. Estrogen therapy prevents or slows down many of the changes associated with skin aging including increasing skin thickness, reduction of wrinkles, increase in the mitotic rate of the epidermis, reduction in the size and activity of the sebaceous gland, reduction in hair growth rate, and stimulation of collagen turnover. See, Creidi et al. Maturitas 19: 211 (1994); Pugliese, Menopausal skin, Skin Inc., March/April: 69-77 (1994).

Incontinence and vulvar and vaginal atrophy have likewise been associated with aging, particularly in post-menopausal women. Stress incontinence is related to weakness of the muscles within the pelvis that provide support for the urethra and the bladder neck. Stress incontinence may be caused by a functional defect or by anatomical defect of the pelvic floor of the tissue or ligaments connecting the vaginal wall with the pelvic muscles. Trauma to pelvic organs or anatomical structures, neurological injury, and some medications may weaken the pelvic function and support. Additionally, women with low estrogen levels may experience stress incontinence due to decreased vaginal muscle tone. Studies have documented that about 50% of all women have occasional incontinence of urine, stool, or flatus requiring medical care or treatment, and as many as 10% have regular incontinence.

Estrogen hormone replacement therapy (HRT) has been used for the chronic treatment of urinary incontinence and vaginal dryness in post-menopausal women. However, poor patient compliance remains problematic and has been noted with HRT because of negative side-effects, such as increased risk of uterine cancer, stroke, heart disease, bloating, increased breast cancer risk, and vaginal bleeding. Non-operative treatment options for patients with incontinence and pelvic support issues can be attempted. But when these exercises fail, surgical repair is often advised. While systemic hormonal therapy remains controversial in the treatment of pelvic floor issues, local target-specific therapy is recognized as efficacious and safe.

Among the many surgical options for incontinence, the introduction into the abdominal cavity of a pubovaginal sling of a synthetic retro-pubic mid-urethral sling has emerged as highly effective. In this procedure, a tape-like material is passed through the pelvic tissue and is positioned around the urethra and the bladder neck, forming a loop located between the urethra and the vaginal wall to create a supportive "hammock" or sling effect. The tape provides an artificial structural support for tissue ingrowth and thereby provides a newly created body tissue supporting means for the urethra. However, there are inherent risks associated with surgery. In addition to the risks associated with anesthesia, surgery also carries the risk of infection at the wound site, problems with wound healing including erosion at the site of sling placement, and potentially excessive bleeding. Additionally, significant post-operative complications have been observed when, for example, synthetic materials are used.

There is a constant need for improved compositions and methods for reducing the signs of skin aging. Moreover, a non-surgical alternative for improving urogenital function would be a boon to medicine.

SUMMARY OF THE INVENTION

The disclosure relates to topical compositions for treating skin conditions associated with aging. In one aspect of the disclosure, a pharmaceutical composition for treating skin aging is provided. The composition can include a pharmaceutically effective amount of estradiol, estriol, hyaluronic acid, and green tea extract for topical administration to the skin. Optionally, the composition additionally includes an effective amount of ascorbic acid. In some aspects of the invention, the composition may also include an effective amount of date palm extract.

Preferably, the pharmaceutical composition further includes a pharmaceutically acceptable carrier such as a cream, gel, lotion, aerosol spray, salve, or infused bandage. Advantageously, the composition is formulated for topical administration. The estriol may be present in an amount between about 0.01 to about 3.0 w/w % of the composition. The pharmaceutically effective amount of estradiol is advantageously between about 0.0001 w/w % and about 3.0 w/w %. The pharmaceutically effective amount of hyaluronic acid may be between about 0.01 w/w % and about 50.0 w/w %. Additionally, the pharmaceutically effective amount of green tea extract may be between about 0.01 and about 10.0 w/w %. The pharmaceutically effective amount of date palm extract may be between about 0.01 and 25 w/w %. Advantageously, the pharmaceutically effective amount of ascorbic acid is preferably between about 0.01 and 10 w/w %. Optionally, the pharmaceutical composition includes estriol at an amount of between about 0.01 to about 3.0 w/w %, estradiol in an amount of between about 0.0001 and 3.0 w/w %, hyaluronic acid in an amount of between about 0.01 and 50 w/w %, and green tea extract in an amount of between about 0.01 to 10.0 w/w %. In certain aspects of the invention, the pharmaceutical composition includes date palm extract in an amount of between about 0.01 and 25 w/w % in addition to estriol, estradiol, hyaluronic acid, and green tea extract in the amounts set forth above. In another aspect of the invention, the pharmaceutical composition includes between about 0.01 and 10.0 w/w % of ascorbic acid in addition to estriol, estradiol, hyaluronic acid, and green tea extract in the amounts set forth above with or without date palm extract. The pharmaceutical composition for treating skin aging may include other ingredients such as a sunscreen, a moisturizer, an exfoliant, a hydroxy acid, a ceramide, glycerin, liposomes, or one or more vitamins.

In still another aspect of the disclosure, a pharmaceutical composition for treating symptoms of skin aging is provided, wherein the composition consists essentially of the following ingredients: an effective amount of estriol; an effective amount of estradiol; an effective amount of hyaluronic acid; an effective amount of green tea extract; and a carrier; wherein the composition is formulated for topical administration.

In yet another aspect of the disclosure, a pharmaceutical composition for treating symptoms of skin aging is provided, wherein the composition consists essentially of an effective amount of estriol, an effective amount of estradiol, an effective amount of hyaluronic acid, an effective amount of green tea extract, an effective amount of date palm extract, and a carrier, wherein the composition is formulated for topical administration. Alternatively, the pharmaceutical composition for treating symptoms of skin aging may consist essentially of an effective amount of ascorbic acid in addition to an effective amount of estriol, estradiol, hyaluronic acid, green tea extract, and optionally, date palm extract.

In another aspect of the disclosure, a method for treating the symptoms of skin aging is provided. The method includes identifying an individual presenting with symptoms of skin aging, and topically administering to that individual a pharmaceutically effective dose of a composition that includes estriol, estradiol, hyaluronic acid, green tea extract, and a pharmaceutically effective carrier. The method may also include administering a pharmaceutically effective amount of date palm extract alone or in combination with ascorbic acid. The amount of date palm extract is preferably between about 0.01 to 25 w/w %. The amount of ascorbic acid is preferably between about 0.01 and 10.0 w/w % of the formulation. The individual may include a post-menopausal female, a pre-menopausal female, or a male. Advantageously, the topical administration of a pharmaceutically effective dose of the present composition treats symptoms of skin aging including rhytids, wrinkles, jowls, sun damage, dull appearance of skin, sagging skin, keratosis, hyperpigmentation, melasma, solar lentigo, solar keratoses, dermatoheliosis, or other skin discoloration disorders associated with aging.

In still another aspect of the disclosure, a method for augmenting the results of cosmetic surgery by topically administering a pharmaceutical composition, which includes estriol, estradiol, hyaluronic acid, green tea extract, and a pharmaceutically acceptable carrier, is provided. Optionally, the method can also include administering glycolic acid. Alternatively or in addition to, the method can also include the administration of date palm extract and/or ascorbic acid. The pharmaceutical composition may be administered to an individual pre-operatively, post-operatively, and/or substantially contemporaneously with a cosmetic surgery.

In another aspect of the disclosure, a cosmetic composition is provided for use in alleviating the effects of skin aging. The cosmetic composition advantageously includes an effective amount of estriol, estradiol, hyaluronic acid, green tea extract and a cosmetically acceptable carrier adapted for topical delivery as a cosmetic product. The cosmetic product may be a makeup product such as a foundation, blush, or lipstick. It may include a colorant such as FD&C Red No. 40 and/or FD&C Yellow No. 5. Optionally, the cosmetic product includes a fragrance, moisturizer, or sunscreen. Advantageously, the cosmetic composition may further include an effective amount of date palm extract and/or ascorbic acid.

In still another aspect of the disclosure, a method for promoting wound healing is described. The method includes topically administering to the surface of a wound a pharmaceutical composition having a pharmaceutically effective amount of estriol; a pharmaceutically effective amount of estradiol; a pharmaceutically effective amount of hyaluronic acid; a pharmaceutically effective amount of green tea extract; and a pharmaceutically acceptable carrier in the amounts described above. Optionally, the pharmaceutical composition further includes an effective amount of date palm extract and/or ascorbic acid.

In yet another aspect of the disclosure, a method of promoting urogenital function is provided. The method includes identifying an individual presenting with symptoms such as incontinence, vulvar atrophy, vaginal atrophy, vaginal dryness, and pelvic floor weakness, and administering intravaginally to the individual a pharmaceutically effective dose of a composition, which includes a pharmaceutically effective amount of estriol, a pharmaceutically effective amount of estradiol, a pharmaceutically effective amount of hyaluronic acid, a pharmaceutically effective amount of green tea extract, and a pharmaceutically acceptable carrier in amounts as described above. The composition may further include a pharmaceutically effective amount of date palm extract. Optionally, the composition may include a pharmaceutically effective amount of ascorbic acid.

In still another aspect of the disclosure, a method of reducing the symptoms of rosacea is described. The method includes identifying an individual suffering from rosacea and topically administering to that individual a pharmaceutically effective dose of a composition which includes a pharmaceutically effective amount of estriol, a pharmaceutically effective amount of estradiol, a pharmaceutically effective amount of hyaluronic acid, a pharmaceutically effective amount of green tea extract, and a pharmaceutically acceptable carrier in amounts as described above. The composition may further include a pharmaceutically effective amount of date palm extract. Optionally, the composition may include a pharmaceutically effective amount of ascorbic acid.

BRIEF DESCRIPTION OF THE DRAWINGS

FIG. 6 is a photograph of a patient presenting with rosacea prior to treatment with the disclosed composition FIG. 7 is a photograph of the patient in FIG. 6 after treatment with the disclosed composition.

DETAILED DESCRIPTION

Figure 1:
FIG. 1 is a photograph of a patient presenting with signs of skin aging prior to the application of the disclosed composition.

This disclosure is directed to compositions and methods for treating skin aging and symptoms related thereto. The disclosure likewise includes a novel composition and method for improving urogenital function. The disclosure is based in part on the surprising discovery that a composition comprising an effective amount of estrogen-like compounds including estriol and estradiol in combination with hyaluronic acid and green tea extract markedly reduces the signs of aging, decreases signs of photoaging, reduces melasma and sunspots, treats solar lentigo, solar kertoses, and dermatoheliosis, increases skin firmness, improves skin elasticity, reduces wrinkle depth, ameliorates the symptoms of rosacea, and improves collagen synthesis and skin moisture. It has further been discovered that ascorbic acid and date palm extract can be added to the formulation to further reduce the signs of aging. The composition is similarly useful for promoting surface wound healing, minimizing scarring and encouraging well-healed scar formation, improving the aesthetics of post-operative scars, facilitating healing in burned and/or traumatized tissues, and reducing stretch marks. Furthermore, the disclosure relates to the unexpected discovery that systemic absorption of the estrogen-like compounds of the composition is surprisingly less when compared to conventional topical estrogen creams.

As used herein, the term "effective amount" means an amount of compound that is capable of treating the symptoms of the described skin aging conditions. "Effective amount" likewise includes an amount of compound that is capable of promoting wound healing and urogenital function. The specific dose of a compound administered according to this invention will, of course, be determined by the particular circumstances surrounding the case including, for example, the compound administered, the route of administration, the state of being of the subject, and the severity of the pathological condition being treated. "Therapeutic agents" as used herein refers to the unique combination of estriol, estradiol, hyaluronic acid, and green tea extract in the amounts described below. "Therapeutic agents", as used herein, can also include ascorbic acid and/or date palm extract.

"Skin", as used herein, refers preferably to the surface of the face and neck. However, the term "skin" refers to any epidermal surface prone to aging and can also include, without limitation, the hands, elbows, upper arm region, knees, thighs, legs, feet, breasts, chest, stomach, buttocks, and back area.

The disclosed composition is an improved anti-aging multi-component formulation for topical administration, which includes estrogen-like compounds, antioxidants, and hyaluronic acid. In certain embodiments, the composition further includes ascorbic acid. In other embodiments, the composition includes date palm extract. We have demonstrated that the topical treatment of skin with estrogen-like compounds reverses some of the changes associated with aging skin. Without being limited to a particular theory, the topical administration of estradiol and estriol is believed to improve skin firmness and elasticity as well as reduce wrinkle depth and pore sizes by stimulating collagen neogenesis. The composition preferably includes between about 0.0001 w/w % to about 3.0 w/w % of estradiol. For example, the effective amount of estradiol is about 0.0001, 0.001, 0.01, 0.015, 0.02, 0.025, 0.05, 1.0, 2.0, or 3.0 w/w % of the composition. Furthermore, the effective amount of estradiol is about 0.01 w/w % of the composition. The effective amount of estriol is preferably between about 0.01 to about 3.0 w/w %. For example, the amount of estriol is between about 0.1 to about 0.3 w/w %.

Also included in the pharmaceutical composition is an effective amount of hyaluronic acid. Without being limited to this mechanism, it has been demonstrated that hyaluronic acid plays an important role in connective tissues such as the skin. The dermis of the skin includes a network of collagen fibers within an interstitial substance composed largely of hyaluronic acid. The elastic properties of hyaluronic acid offer resistance to compression, so that the skin protects underlying structures against damage. At the same time, hyaluronic acid allows the collagen fibers to move easily through the interstitial space and allows collagen fiber to deposit. As individuals age, the levels of hyaluronic acid in the skin diminish as the skin cells lose their ability to produce hyaluronic acid. Hyaluronic acid's absorption abilities and large molecular structure allow the epidermis to achieve greater suppleness and proper skin plasticity. Typically, the amount of hyaluronic acid in the disclosed compositions is between about 0.01 w/w % to about 50.0 w/w % of the formulation. The amount of hyaluronic acid can be about 0.1%, 0.2%, 0.3%, 0.5%, 1.0%, 1.5%, 2.0%, 2.5%, 3.0%, 3.5%, 4.0%, 4.5%, 5%, 7.0%, 10, % 15%, 20%, 30%, 40%, or 50 w/w %. For instance, hyaluronic acid is present in an amount of about 0.2% w/w of the composition.

The pharmaceutical composition similarly includes an effective amount of green tea extract. The antioxidant polyphenols in green tea extract are believed to reverse sun damage. The amount of green tea extract in the formulation is preferably between about 0.01 to 10.0 w/w %. The amount of green tea extract can be about 0.01, 0.05, 0.01, 0.2, 0.25, 0.4, 0.6, 0.8, 1.0, 2.0, 3.0, 4.0, 5.0, 6.0, 7.0, 8.0, 9.0, or 10.0 w/w %. For example, the amount of green tea extract is 0.2 w/w % of the composition.

In one embodiment, the pharmaceutical composition optionally includes an effective amount of date palm extract. Hormones play a central role in skin appearance and are implicated in skin aging. Date palm kernel is rich in phytohormones and exhibits a significant anti-wrinkle effect when applied topically. The amount of date palm extract is preferably between about 0.01 and 25 w/w %. In a preferred embodiment, the date palm extract is present in an amount of approximately 5.0 w/w % of the formulation. For instance, the amount of date palm extract is 0.01, 0.1, 0.5, 1.0, 2.0, 5.0, 7.0, 10, 15, 20, or 25 w/w % of the formulation.

In another embodiment, the pharmaceutical composition can include an effective amount of ascorbic acid. Considering the apparent central role that reactive oxygen free-radicals play in the genesis of cutaneous photoaging, it is believed that a topical free-radical scavenger would be a useful in preventing and/or treating the signs of aging. In addition to the protection mediated against UV light by the ascorbic acid, ascorbic acid has been shown to produce stimulation of both Type I and Type III collagen in a cultured human fibroblast model. Without being bound to a particular theory, it is hypothesized that L-ascorbic acid stimulates procollagen synthesis without appreciably altering noncollagen synthesis. Moreover, ascorbic acid may be an important regulator of three different procollagen genes and works by promoting hydroxyproline formation and procollagen synthesis. Furthermore, L-ascorbic acid has also been shown to stimulate human fibroblast proliferation. The effective amount of ascorbic acid is preferably between 0.01 w/w % and 10.0 w/w % of the composition. For example, the effective amount of ascorbic acid is about 0.01, 0.02, 0.03, 0.04, 0.05, 0.075, 0.1, 0.5, 1.0, 2.0, 3.0, 4.0, 5.0, 6.0, 7.0, 8.0, 9.0, or 10.0 w/w %.

In still another embodiment, the pharmaceutical composition optionally includes an effective amount of a topical resurfacing agent. One example of a suitable topical resurfacing agent is glycolic acid. Without being limited to a particular mechanism, it is believed that glycolic acid, an alpha hydroxy acid, is useful in treating skin aging by acting as an exfoliant to remove old, damaged cells on the top layer of skin and as a result it smoothes and softens the skin, diminishes fine lines, decreases acne outbreaks, evens out coloration and lightens hyperpigmented areas. The effective amount of topical resurfacing agent is preferably between 1.0 w/w % and 20 w/w %. In a preferred embodiment, the effective amount of topical resurfacing agent is between about 10 and 15 w/w % of the formulation. For instance, the amount of topical resurfacing agent is 10, 11, 12, 13, 14, or 15 w/w % of the formulation.

In another embodiment, a method for promoting wound healing is provided. We have discovered that the administration of a composition comprising the therapeutic agents set forth above accelerates surface wound healing time, improves the aesthetics of a scar, and promotes the maturation of scars. As used herein, the term "wound" includes, without limitation, an injury to the body (as from violence, accident, or surgery) that involves laceration or breaking of a membrane and usually damage to underlying tissues. The term "wound" further includes burns and post-surgical incisions. The method includes topically administering a composition comprising an effective amount of estradiol, estriol, hyaluronic acid, and green tea extract in amounts as set forth above at the site of a wound. In a preferred embodiment, the composition further includes an effective amount of ascorbic acid. In another embodiment, the composition includes an effective amount of date palm extract. In yet another embodiment, the composition includes an effective amount of date palm extract and ascorbic acid.

In one embodiment, the composition is administered topically to the epidermis to promote wound healing. In another embodiment, the instant composition is administered topically to the vagina, vulva, or perineum to accelerate the healing of vaginal trauma. For example, the present invention is useful in treating trauma associated with an episiotomy or vaginal tearing associated with childbirth. Additionally, the composition can be applied to improve the surgical outcome of a patient undergoing pelvic, vulvar, and/or perineal surgery. The composition can be used to improve prolapse and incontinence issues.

A method of augmenting plastic surgery is similarly provided. As used herein, the phrase "plastic surgery" includes, without limitation, rhytidectomy and rhytidoplasty as well as more minor procedures such as cheek pad lifts (midface lift) and less invasive temporal lifts (lateral brow lifts). Also included within the meaning of plastic surgery is surgery to the eye area such as blepharoplasty, Botox® (Botulinum Toxin A), cathopexy, chemical peel, treatment of dark under-eye circles, fat grafting, LASER resurfacing, micropigmentation, NLite LASER, PhotoDerm/FotoFacial, SOOF lift (sub-orbicularis oculi fat repositioning), tattoo removal (cosmetic), and temporal lift. Also included within the meaning of "plastic surgery" is facial contouring such as buccal fat extraction, cheek augmentation, chin augmentation, facial liposuction, fat grafting, injectable fillers for tissue augmentation, jaw augmentation or reduction, lip augmentation or reduction, and nose surgery. Facial rejuvenation procedures are similarly encompassed within the meaning of "plastic surgery" and include, without limitation, BOTOX®, brow and/or forehead lift, chemical peel, dermabrasion, face lift, fat grafting, injectable fillers, LASER resurfacing, lip lifting and rejuvenation, lip lifting and rejuvenation, microdermabrasion, nasolabial fold correction, PhotoDerm/FotoFacial, temporal lift, and APTOS® thread lift. Neck and skincare treatments as well as other procedures designed to improve the youthful appearance of an individual are similarly included within the meaning of "plastic surgery." Exemplary neck and skincare treatments include, without limitation, BOTOX®, chemical peels, LASER resurfacing, neck lift (or platysmaplasty), submental liposuction, acne scar removal, acne treatment, color corrective cosmetics, physician skin care, hyperpigmentation removal, and microdermabrasion. Other procedures such as micropigmentation, otoplasty, scar revision/keloid prevention, and tattoo removal are likewise included within the meaning of "plastic surgery."

The method of augmenting plastic surgery comprises topically administering to an individual having plastic surgery an effective amount of a pharmaceutical composition comprising estriol, estradiol, hyaluronic acid, and green tea extract formulated with a pharmaceutically acceptable carrier as will be described in greater detail below. In certain embodiments, the pharmaceutical composition further includes an effective amount of date palm extract and/or ascorbic acid. It will be appreciated that the pharmaceutical composition can be topically applied pre-operatively, substantially contemporaneously with the surgery, and/or post-operatively. As will be described in greater detail below, the composition can be applied directly to the skin as a cream, gel, ointment, lotion, salve, or aerosol spray. In certain embodiments, the mode of delivery of the carrier containing the therapeutic agents includes but is not limited to a smear, spray, a time-release patch, a liquid absorbed wipe, and combinations thereof. In one embodiment, the therapeutic agents including estrogens, hyaluronic acid, green tea extract, and optionally date palm extract with or without ascorbic acid can be applied to a bandage either directly or in a carrier. The bandages may be prepared damp or dry, wherein the therapeutic agents are in a lyophilized form on the bandage. The carriers of the compositions of the present invention may comprise semi-solid and gel-like vehicles that include a polymer thickener, water, preservatives, active surfactants or emulsifiers, antioxidants, sun screens, and a solvent or mixed solvent system. Osborne, U.S. Pat. No. 5,863,560, issued on Jan. 26, 1999, hereby incorporated by reference, discusses a number of different carrier combinations which can aid in the exposure of the skin to a medicament. In certain embodiments, the carrier is a silicone-impregnated tape or dressing such as Silicone N-A from Johnson & Johnson Medical Ltd. (Ascot, Windsor and Maidenhead, UK).

Without being bound to a particular theory, it is believed that the disclosed compositions promote collagen neogenesis and reduces tissues inflammation, and improves tissue hydration. As such, the compositions are useful to treat a number of skin conditions in addition to treating symptoms of skin aging. For example, as described above, the present compositions can be employed to promote surface wound healing associated with surgery, trauma, and burns. More particularly, the promotion of scar care, aesthetic improvement of post-operative scar formation, and maturation of wound healing are specifically contemplated. Similarly, the compositions provide a method of reducing scars, preventing keloid scar formation, and accelerating wound healing times. Additionally, the compositions provide a method of reducing the appearance of stretch marks on the surface of the skin.

A composition and method for the treatment of rosacea is provided. Rosacea is a chronic skill disease that can cause red patches, lines, and small pimples on the face, increased heat, increased capillaries, as well as burning and irritation in the eyes and eyelids. Untreated rosacea can progress and eventually cause larger, disfiguring bumps on the nose, rhinophyma, and papules on the face and serious eye problems. The composition includes an effective amount of estradiol, estriol, hyaluronic acid, green tea extract, and optionally, ascorbic acid with or without date palm extract in the amounts detailed above and a pharmaceutically acceptable carrier. A method of treating an individual suffering from rosacea includes identifying an individual suffering from rosacea and topically administering to that individual an effective amount of the disclosed composition.

Formulations

For the treatment of rhytids or skin wrinkles, a preferred method of administration of the pharmaceutical and cosmetic composition is by topical application. The topical pharmaceutical and cosmetic compositions of the present invention may be made into a wide variety of product types. These include, but are not limited to lotions, creams, beach oils, gels, sticks, sprays, ointments, pastes, mousses and cosmetics. These product types may comprise several types of pharmaceutical or cosmetic carrier systems including, but not limited to solutions, emulsions, gels and solids. The topical pharmaceutical and cosmetic compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dissolved therein the anti-wrinkle estriol and estradiol, and possesses acceptable safety properties (e.g., irritation and sensitization characteristics). One example of a suitable pharmaceutically acceptable aqueous solvent is distilled water. Examples of a suitable pharmaceutically acceptable organic solvent include, for example, monohydric alcohols, such as ethanol, and polyhydric alcohols, such as glycols. If the topical pharmaceutical and cosmetic compositions of the present disclosure are formulated as an aerosol and applied to the skin as a spray-on, a propellant is added to a solution composition. Examples of propellants useful herein include, but are not limited to, the chlorinated, fluorinated and chlorofluorinated lower molecular weight hydrocarbons. A more complete disclosure of propellants useful herein can be found in Sagarin, Cosmetics Science and Technology, 2nd Edition, Vol. 2, pp. 443-465 (1972), hereby incorporated by reference in its entirety.

In one embodiment, topical pharmaceutical and cosmetic compositions of the present invention further comprise a suitable amount of a topical pharmaceutical and cosmetically-acceptable emollient. As used herein, "emollients" refer to materials used for the prevention or relief of dryness, as well as for the protection of the skin. Wide varieties of suitable emollients are known and may be used herein. Sagarin, Cosmetics, Science and Technology, 2nd Edition, Vol. 1, pp. 32-43 (1972), contains numerous examples of suitable materials. Examples of classes of useful emollients include hydrocarbon oils and waxes such as mineral oil, petrolatum, paraffin, ceresin, ozokerite, microcrystalline wax, polyethylene, and perhydrosqualene; silicone oil, such as dimethyl polysiloxanes, methylphenyl polysiloxanes, and water-soluble and alcohol-soluble silicone glycol copolymers. Other suitable emollients include triglyceride esters such as vegetable and animal fats and oils including castor oil, safflower oil, cotton seed oil, corn oil, olive oil, cod liver oil, almond oil, avocado oil, palm oil, sesame oil, and soybean oil; acetoglyceride esters, such as acetylated monoglycerides; ethoxylated glycerides, such as ethoxylated glycerylmonostearate; alkyl esters of fatty acids including methyl, isopropyl, and butyl esters of fatty acids, alkyl esters including hexyl laurate, isohexyl laurate, iso-hexyl palmitate, isopropyl palmitate, decyl oleate, isodecyl oleate, hexadecyl stearate, decyl stearate, isopropyl isostearate, diisopropyl adipate, dissohexyl adipate, di-hexyldecyl adipate, di-isopropyl sebacate, lauryl lactate, myristyl lactate, and cetyl lactate; and alkenyl esters of fatty acids such as oleyl myristate, oleyl stearate, and oleyl oleate. Other suitable classes of emollients include fatty acids such as pelargonic, lauric, myristic, palmitic, stearic, isostearic, hydroxystearic, oleic, linoleic, ricinoleic, arachidic, behenic, and erucic acids.; fatty alcohols such as lauryl, myristyl, cetyl, hexadecyl, stearyl, isostearyl, hydroxystearyl, oleyl, ricinoleyl, behenyl, and erucyl alcohols, as well as 2-octyl dodecanol; fatty alcohol ethers; ethoxylated fatty alcohols; ether-esters such as fatty acid esters of ethoxylated fatty alcohols; lanolin and derivatives including lanolin oil, lanolin wax, lanolin alcohols, lanolin fatty acids, isopropyllanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysis of lanolin, ethoxylated hydrogenated lanolin, ethoxylated sorbitol lanolin, and liquid and semisolid lanolin absorption bases are illustrative of emollients derived from lanolin; polyhydric alcohols and polyether derivatives such as propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide]homopolymers (100,000-5,000,000), polyalkylene glycols and derivatives, hexylene glycol(2-methyl-2,4-pentanediol), 1,3-butylene glycol, 1,2,6-hexanetriol, ethohexadiol USP (2-ethyl,3-hexanediol), C15-C18 vicinal glycol, and polyoxypropylene derivatives of trimethylolpropane; polydydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylatedpropylene glycol monostearate, glyceryl mono- and di-fatty acid esters, polyglycerol poly-fatty acid esters, ethoxylated glyceryl monostearate, 1,3-butylene glycol-monostearate, 1,3-butylene glycol distearate, polyoxyethylene polyol fatty acid ester, sorbitan fatty acid esters, and polyoxyethylene sorbitan fatty acid esters; wax esters such as beeswax, spermaceti, myristyl myristate and stearyl stearate; beeswax derivatives, e.g., polyoxyethylene sorbitol beeswax; vegetable waxes including carnauba and candelilla waxes; and phospholipids, such as lecithin and derivatives; sterols including, for example, cholesterol and cholesterol fatty acid esters; amides such as fatty acid amides, ethoxylated fatty acid amides and solid fatty acid alkanolamides. Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol.

Alternatively, the composition can be formulated as a lotion. A lotion can be made from a solution carrier system. Lotions typically comprise from about 0.01 to about 3.0 w/w % estriol, between about 0.0001 to about 3.0 w/w %, for example 0.01 w/w % of estradiol, from about 0.01% to about 50 w/w %, for example about 0.2 w/w %, of hyaluronic acid, and between about 0.01 and 10.0 w/w % of green tea extract. In a preferred embodiment, the lotion further includes between about 0.01 to about 25 w/w % of date palm extract. In a particularly preferred embodiment, the lotion can include between about 0.01 to about 10.0 w/w % of ascorbic acid, for example 0.1 w/w %. In some embodiments, the lotion includes from about 1% to about 20%, for example, from about 5% to about 10%, of an emollient; and from about 50% to about 90%, for example, from about 60% to about 80% of water.

Another type of product that may be formulated from a solution carrier system is a cream. A cream of the present disclosure comprises from about 0.01 to about 3.0 w/w % estriol, between about 0.0001 to about 3.0 w/w %, for example, 0.01 w/w % of estradiol, from about 0.01 to about 50 w/w %, for example, about 0.2 w/w %, of hyaluronic acid, and between about 0.01 and 10.0 w/w % of green tea extract, for example 0.2 w/w %; from about 5% to about 50%, for example, from about 10% to about 20%, of an emollient, and from about 45% to about 85%, preferably from about 50% to about 75% of water. In a preferred embodiment, the cream further includes between about 0.01 to about 25 w/w % of date palm extract. In a particularly preferred embodiment, the lotion can include between about 0.01 to about 10.0 w/w % of ascorbic acid.

Yet another type of product that may be formulated from a solution carrier system is an ointment. An ointment can comprise a simple base of animal or vegetable oils or semi-solid hydrocarbons (oleaginous). Ointments can also include absorption ointment bases which absorb water to form emulsions. Optionally, the ointment carriers may be water soluble. An ointment can include from about 2% to about 10% of an emollient plus from about 0.1% to about 2% of a thickening agent. Examples of suitable thickening agents include: cellulose derivatives (e.g., methyl cellulose and hydroxy propylmethylcellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (CARBOPOLS®; sold by B.F. Goodrich Company, such polymers are described in detail in Brown, U.S. Pat. No. 2,798,053, issued Jul. 2, 1957). A more complete disclosure of thickening agents useful herein can be found in Sagarin, Cosmetics, Science and Technology, 2nd Edition, Vol. 1, pp. 72-73 (1972). If the carrier is formulated as an emulsion, from about 1% to about 10%, for instance, from about 2% to about 5%, of the carrier system comprises an emulsifier. Suitable emulsifiers include nonionic, anionic or cationic emulsifiers. Exemplary emulsifiers are disclosed in, for example, McCutcheon's Detergents and Emulsifiers, North American Edition, pages 317-324 (1986). Preferred emulsifiers are anionic or nonionic, although other types can also be employed.

Lotions and creams can be formulated as emulsions as well as solutions. Typically, such lotions comprise from about 0.01 to about 3.0 w/w % estriol, for example, 0.2 w/w %, between about 0.0001 to about 3.0 w/w %, preferably 0.01 w/w % of estradiol, from about 0.1 to about 50 w/w %, more preferably about 0.2 w/w %, of hyaluronic acid, and between about 0.01 and 10.0 w/w % of green tea extract; from about 1% to about 20%, for example, from about 5% to about 10%, of an emollient; from about 25% to about 75%, for instance, from about 45% to about 95%, water; and from about 0.1% to about 10%, for example, from about 0.5% to about 5%, of an emulsifier. Such creams would typically comprise from about 0.01 to about 3.0 w/w % estriol, for instance, 0.2 w/w %, between about 0.0001 to about 3.0 w/w %, for instance, 0.01 w/w % of estradiol, from about 0.01 to about 50 w/w %, for example, about 0.2 w/w %, of hyaluronic acid, and between about 0.01 and 10.0 w/w % of green tea extract of the anti-skin aging composition; from about 1% to about 20%, for example, from about 5% to about 10%, of an emollient; from about 20% to about 80%, for instance, from about 30% to about 70%, water; and from about 1% to about 10%, for example, from about 2% to about 5%, of an emulsifier. In a preferred embodiment, the cream further includes between about 0.01 to about 25 w/w % of date palm extract. In a particularly preferred embodiment, the cream can include between about 0.01 to about 10.0 w/w % of ascorbic acid.

Single emulsion skin care preparations, such as lotions and creams, of the oil-in-water type and water-in-oil type are well known in the cosmetic arts and are useful in the present embodiments. One example of a suitable emulsion for use in the present compositions is an oil-in-water emulsion such as Dermabase Cream™ (Paddock Laboratories, Inc., Minneapolis, Minn.). Multiphase emulsion compositions, such as the water-in-oil-in water type are also useful in the present embodiments. In general, such single or multiphase emulsions contain water, emollients and emulsifiers as essential ingredients. Triple emulsion carrier systems comprising an oil-in-water-in-silicone fluid emulsion composition are also useful in the present embodiments.

Another emulsion carrier system useful in the topical pharmaceutical and cosmetic compositions of the present disclosure is a microemulsion carrier system. Such a system preferably comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with the therapeutic agents described above.

If the topical pharmaceutical and cosmetic compositions of the present disclosure are formulated as a gel or a cosmetic stick, a suitable amount of a thickening agent, as disclosed supra, is added to a cream or lotion formulation. The topical pharmaceutical and cosmetic compositions of the present disclosure may also be formulated as makeup products such as foundations, blush, and lipstick and can contain conventional cosmetic adjuvants, such as dyes, opacifiers, pigments and perfumes. Foundations are solution or lotion-based with appropriate amounts of thickeners such as algin, xanthan gum, cellulose gum, cocamide DEA, guar gum lanolin alcohol, paraffin, and propylene glycol, pigments including ultramarine blue, titanium dioxide, and carmine, colorants such as FD&C Red No. 40 and FD&C Yellow No. 5, moisturizers, and fragrance. Optionally, the foundation can include a sunscreen agent. The topical pharmaceutical and cosmetic compositions of the present disclosure may contain, in addition to the aforementioned components, a wide variety of additional oil-soluble materials and/or water-soluble materials conventionally used in topical compositions, at their established levels. Various water-soluble materials may also be present in the compositions of this invention. These include humectants, such as glycerol, sorbitol, propylene glycol, alkoxylated glucose and hexanetriol, ethyl cellulose, polyvinylalcohol, carboxymethyl cellulose, vegetable gums and clays such as VEEGUM® (magnesium aluminum silicate, R. T. Vanderbilt, Inc.); proteins and polypeptides, preservatives such as the methyl, ethyl, propyl and butyl esters of hydroxybenzoic acid (Parabens® Mallinckrodt Chemical Corporation), EDTA, methylisothiazolinone and imidazolidinyl ureas (Germall 115®—Sutton Laboratories); and an alkaline agent such as sodium hydroxide or potassium hydroxide to neutralize, if desired, part of the fatty acids or thickener which may be present.

The topical pharmaceutical and cosmetic compositions of the present disclosure can also include a safe and effective amount of a penetration enhancing agent. A preferred amount of penetration enhancing agent is from about 1% to about 5% of the composition. Other conventional skin care product additives may also be included in the compositions of the present invention. For example, collagen, elastin, hydrolysates, primrose oil, jojoba oil, epidermal growth factor, soybean saponins, mucopolysaccharides, and mixtures thereof may be used. Various vitamins can also be included in the compositions of the present invention. For example, Vitamin A, and derivatives thereof, Vitamin B2, biotin, pantothenic, Vitamin D, and mixtures thereof can be used.

In some embodiments, the composition comprising estradiol, estriol, hyaluronic acid, and green tea extract is incorporated into anti-wrinkle skin cleaning compositions. The skin cleaning compositions comprise a cosmetically acceptable surfactant in addition to the anti-wrinkle multi-component formulation including estradiol, estriol, hyaluronic acid, and green tea extract. The anti-wrinkle multi-component formulation can, in some embodiments, additionally include an effective amount of ascorbic acid, date palm extract, or combinations thereof. The term "cosmetically-acceptable surfactant" refers to a surfactant which is not only an effective skin cleanser, but also can be used without undue toxicity, irritation, allergic response, and the like. Furthermore, the surfactant should be capable of being commingled with the anti-wrinkle components in a manner such that there is no interaction which would substantially reduce the efficacy of the composition for treating wrinkles in mammalian skin. In addition to the cosmetically effective amounts of the active ingredients, the skin cleaning compositions of the present disclosure contain from about 1% to about 90%, preferably from about 5% to about 10%, of a cosmetically-acceptable surfactant. The physical form of the skin cleansing compositions is not critical. The compositions can be, for example, formulated as toilet bars, liquids, pastes, or mousses. Toilet bars are most preferred since this is the form of cleansing agent most commonly used to wash the skin. The surfactant component of the disclosed compositions is selected from the group consisting of anionic, nonionic, zwitterionic, amphoteric and ampholytic surfactants, as well as mixtures of these surfactants. Such surfactants are well known to those skilled in the detergency art. The cleaning compositions of the present disclosure can optionally contain, at their art-established levels, materials which are conventionally used in skin cleansing compositions.

"Cosmetically-acceptable" carrier refers to a carrier that can be used without undue toxicity, skin irritation, allergic response, and the like. Furthermore, the cosmetically acceptable carrier should be capable of being commingled with the anti-wrinkle active ingredients in a manner such that there is no interaction which would substantially reduce the efficacy of the composition for treating wrinkles in mammalian skin.

Other skin care products for the treatment of skin wrinkles may contain combinations of additional active ingredients. Such combinations include, for example, sunscreens and sunblocks. Optimum regulation of skin wrinkling resulting from exposure to U.V. light can be obtained by using a combination of the composition comprising estriol, estradiol, hyaluronic acid, and green tea extract of the present invention together with sunscreens or sunblocks. Useful sunblocks include, for example, zinc oxide and titanium dioxide. Photo damage is a predominant cause of skin wrinkling. Thus, for purposes of wrinkle prevention, the combination of the disclosed compositions with a UVA and/or UVB sunscreen would be most desirable. The inclusion of sunscreens in compositions of the present invention will provide immediate protection against acute UV damage. Thus, the sunscreen will prevent further wrinkle formation caused by UV radiation, while the anti-wrinkle agents treat existing wrinkles and skin atrophy.

A wide variety of conventional sunscreening agents are suitable for use in combination with the anti-wrinkle formulations. Sagarin, et al., at Chapter VII, pages 189 et seq., of Cosmetics Science and Technology, disclose numerous suitable agents. Specific suitable sunscreening agents include, for example: p-aminobenzoic acid, its salts and its derivatives (ethyl, iso-butyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropylene glycol esters); cinnamic acid derivatives (methyl and benzyl esters, .alpha.-phenyl cinnamonitrile; butyl cinnamoyl pyruvate); dihydroxycinnamic acid derivatives (umbelliferone, methyl umbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyidisulfonates; (7-hydroxy, 7-methyl, 3-phenyl); diazoles(2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol)(6-propyl piperonyl)ether; hydroquinone; benzophenones (oxybenzene, sulisobenzone, dioxybenzone, benzoresorcinol, 2,2',4,4'tetrahydroxy-benzophenone, 2,2'-dihydroxy-4,4'-dimethoxybenzophenone, octabenzone; 4-isopropyidibenzoyl-methane; butylmethoxy dibenzoylmethane; etocrylene; and 4-isopropyl-dibenzoylmethane). Mixtures of sunscreen compounds may be used to optimize the desired sunscreen properties of the formulation. A safe and effective amount of sunscreen may be used in the compositions of the present invention. The sun-screening agent must be compatible with the anti-wrinkle agents. Generally the composition may comprise from about 1% to about 20%, preferably from about 2% to about 10%, of a sunscreening agent. Exact amounts will vary depending upon the sunscreen chosen and the desired Sun Protection Factor (SPF). An agent may also be added to any of the compositions of the present invention to improve the skin substantivity of those compositions, particularly to enhance their resistance to being washed off by water, or rubbed off The disclosed compositions can also include anti-oxidants or free radical scavengers. In a preferred anti-aging composition of the present invention, an antioxidant/radical scavenger is included as an active agent along with the estrogen, hyaluronic acid, and green tea extract components. The inclusion of an anti-oxidant/radical scavenger increases the wrinkle treating benefits of the composition. A safe and effective amount of an anti-oxidant/radical scavenger may be added to the compositions of the present invention, preferably from about 0.1% to about 10%, more preferably from about 1% to about 5%, of the composition. Antioxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2 carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N diethylhydroxylamine, amino-guanidine), sulfhydryl compounds (e.g., glutathione), and dihydroxy fumaric acid and its salts maybe used.

In another embodiment, the disclosed compositions include a chelating agent as an active agent along with the anti-aging estrogens, hyaluronic acid, and green tea extract. As used herein, "chelating agent" means an active agent capable of removing a metal ion from a system by forming a complex so that the metal ion cannot readily participate in or catalyze chemical reactions. The inclusion of a chelating agent increases the anti-aging benefits of the composition. A safe and effective amount of a chelating agent maybe added to the compositions of the present invention, for example, from about 0.1% to about 10%, specifically from about 1% to about 5%, of the composition. Preferred chelators useful in compositions of the present invention are furildioxime and derivatives thereof, more preferably amphi-2-furildioxime.

In another embodiment, the disclosed anti-skin aging compositions can include a retinoid, preferably retinoic acid, as an active agent. A safe and effective amount of a retinoid may be added to the compositions of the present invention, preferably from about 0.001% to about 2%, more preferably from about 0.01% to about 1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

The present disclosure further relates to a method for treating signs of aging in mammalian skin. As used herein, "skin aging" refers to skin conditions associated with aged skin including, without limitation, wrinkles, rhytids, sun damage, dull appearance of the skin, sagging skin, jowls, keratosis, melasma, and hyperpigmentation. Such a method comprises treating the skin with an effective amount of a composition comprising estriol, estradiol, hyaluronic acid, and green tea extract as defined above. The amount of therapeutic agents and frequency of treatment will vary widely depending upon the level of wrinkling already in existence in the subject, the rate of further wrinkle formation, and the level of regulation desired.

The present disclosure further provides a method for treating photo-aging. As used herein, the term "photo-aging" includes, without limitation, aging of the skin associated with exposure to the sun or other ultraviolet energy sources. Symptoms of photo-aging include, for example, solar lentigo (age spots), solar keratoses, and dermatoheliosis. The method of treating photo-aging includes topically administering to an individual in need thereof a composition comprising an effective amount of a composition comprising estriol, estradiol, hyaluronic acid, and green tea extract as defined above. The method can optionally include the administration of an effective amount of ascorbic acid and/or date palm extract.

One method of treating the skin is via topical application of a safe and effective amount of the therapeutic agents to treat wrinkles in mammalian skin. The frequency of topical application to the skin can vary widely, depending upon personal needs, but it is suggested as an example that topical application range from about once per week to about 10 times daily, preferably from about twice per week to about 4 times daily, more preferably from about 3 times a week to about twice daily, most preferably about once per day. The period of topical application would preferably be over a period of from about one month to about ten years.

Advantageously, the present disclosure also provides kits for use by a consumer for treating skin aging. The kits comprise a) a pharmaceutical composition comprising effective amounts of estradiol, estriol, hyaluronic acid, and green tea extract and a pharmaceutically acceptable carrier; and b) instructions describing a method of using the pharmaceutical composition for treating skin wrinkles, other conditions associated with skin aging, and/or wound healing. In some embodiments, the kit also includes an effective amount of glycolic acid. In another embodiment, the pharmaceutical composition further includes an effective amount of ascorbic acid, date palm extract, or combinations thereof A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

In another embodiment, a composition and method for promoting urogenital function is provided. As used herein, the phrase "promoting urogenital function" includes the treatment of stress incontinence, urge incontinence, pelvic floor weakness, interstitial cystitis, loss of glycoamino glycan, and vaginal and vulvar atrophy including itching, burning, dryness in or around the vagina, difficulty or burning on urination, particularly in peri-menopausal or post-menopausal women. Also included within the meaning of "promoting urogenital function" is the reduction of moderate or severe menopausal symptoms including warmth in the face, neck, and chest, or sudden intense episodes of heat and sweating.

The disclosed compositions are similarly useful in treating certain conditions in which a young woman's ovaries do not produce enough estrogen naturally. The treatment of certain types of abnormal vaginal bleeding due to hormonal imbalance, cancers, and osteoporosis is likewise contemplated herein. The promotion of urogenital function further includes the improvement of surgical outcome for pelvic, vulva, and perineal surgery as well as post-surgical outcome for prolapse and urinary incontinence.

The method of promoting urogenital function includes administering intravaginally an effective dose of a composition comprising an effective amount of estriol, estradiol, green tea extract, and hyaluronic acid. In some embodiments, the composition further includes an effective amount of ascorbic acid, date palm extract, or combinations thereof. It is understood that the dosage, regimen, and mode of administration of these therapeutic agents will vary according to the malady and the individual being treated and will be subject to the judgment of the medical practitioner involved. It is preferred that the administration of the therapeutic agents begin at a low dose and be increased until the desired effects are achieved. For effective administration of the therapeutic agents, the composition comprising estriol, estradiol, green tea extract, hyaluronic acid, and optionally, ascorbic acid, date palm extract, or combinations thereof with a pharmaceutical carrier is formulated as a lotion, cream, foam, suspension, solution, or suppository. In a preferred embodiment, the therapeutic agents are formulated with a pharmaceutical carrier as a cream. Preferably, an individual presenting with impaired urogenital function is administered 0.5 grams, 1 gram, 2 grams, 3 grams, 4 grams or 5 grams of cream comprising the therapeutic agents in the amounts detailed below. Administration can be once a day, once every other day, or once a week, depending upon the malady to be treated and severity thereof. In a preferred embodiment, the individual is administered the disclosed composition between three and four times a week until the symptoms are resolved.

The composition for promoting urogenital function includes 0.01 to about 3.0 w/w % estriol, for example 0.01 w/w % estriol, between about 0.0001 to about 3.0 w/w %, preferably 0.2 w/w % of estradiol, from about 0.01 to about 50 w/w %, more preferably between about 0.1 to about 5.0 w/w %, of hyaluronic acid, and between about 0.01 and 10.0 w/w % of green tea extract. Optionally, the composition further includes between about 0.01 to about 25 w/w % of date palm extract. In a particularly preferred embodiment, the composition can include between about 0.01 to about 10.0 w/w % of ascorbic acid. The therapeutic agents including estriol and estradiol can be administered according to the regimens and doses known in the art. In a preferred embodiment, the therapeutic agents are formulated as a cream adapted for delivery into the vagina and further include from about 5% to about 50%, preferably from about 10% to about 20%, of an emollient, and from about 45% to about 85%, preferably from about 50% to about 75%, water. Alternatively, the composition can be formulated as a suppository. In addition to the active therapeutic agents discussed above, suppository formulations can include traditional materials such as cocoa butter, with or without the addition of waxes to alter the suppository's melting point, and glycerin. Water soluble suppository bases, such as polyethylene glycols of various molecular weights, are likewise suitable for use in formulating the therapeutic agents for vaginal delivery.

Examples

The following examples teach various protocols for treating signs and symptoms of skin aging with the disclosed anti-aging compositions. Additionally, the examples teach the use of the disclosed compositions for promoting wound healing, reducing the signs of photo-aging, treating rosacea, and improving urogenital function. These examples are illustrative only and are not intended to limit the scope of the claims. The treatment methods described below can be optimized using empirical techniques well known to those of ordinary skill in the art. Moreover, artisans of ordinary skill would be able to use the teachings described in the following examples to practice the full scope of the claims.

Example 1

Clinical Trial Relating to the Administration of Topical Cream to Treat Symptoms of Aging To study the effects of estriol, estradiol, hyaluronic acid, and green tea extract on human skin, histological changes, including elasticity and epidermal and dermal thickness as well as clinical changes in skin appearance were evaluated. Additionally, as will be described in greater detail with reference to Example 2, systemic hormonal levels of estriol and estradiol were measured.

Twelve patients were enrolled in the study, including three males and nine females. The patients' ages range from about 38 to about 74 years of age with moderate to severe clinical signs of facial aging. Patients were screened for contraindications to estrogen and any patient with a history of breast cancer or melanoma were excluded from the study.

Prior to initiation of treatment, patients underwent a hairline skin biopsy to evaluate their baseline epidermal and dermal thickness and skin architectural characteristics. Standardized high-resolution photos of the facial rhytids were obtained. A topical formulation comprising 0.02 w/w % estriol, 0.01 w/w % estradiol, and 0.2% hyaluronic acid was professionally compounded in Dermabase Cream™ (Paddock Laboratories, Minneapolis, Minn.) as a white cream, which is stable at room temperature. Estriol and estradiol are commercially available from, for example, Gallieop Pharmaceutical of Minnesota. The hyaluronic acid is available through, for example, Spectrum Chemical of Texas. The formulation also included 0.2 w/w % green tea extract.

Patients were instructed to apply the cream to their entire face and hands daily. The treatment continues for four months. At the end of the four month clinical trial, punch biopsies were performed and changes in dermal and epidermal thickness and vascularity were evaluated. Specifically, changes in epidermal thickness, collagen density, elastic fibers, keratosis, cellular atypia and rete peg patterns were noted. High resolution photographs were taken for comparison. Facial mask determinations of skin changes were also performed.

Figure 2:
FIG. 2 is a photograph of the patient in FIG. 1 after completing the four month clinical trial described in Example 1 below.

In addition to histological analysis, the impact of the composition in reducing signs of aging was evaluated clinically. Turning to the Figures, FIG. 1 represents a photograph of a patient taken at the beginning of the clinical trial. Notably, the patient presented with multiple rhytids, particularly around the eye area. Additionally, sun damage, solar lentigo, loss of elasticity, and areas of keratoses were observed on the patient's face. At the conclusion of the four month clinical trial, a reduction in wrinkle depth, improvement in skin tone, reduction of facial rhytids, diminished areas of solar lentigos, and imporvemtn in skin turgor and tightening of the pores of the were observed as evidenced in FIG. 2. FIG. 2 is a photograph of the same patient in FIG. 1 upon completion of the clinical trial. The topical administration of the cream comprising estradiol, estriol, hyaluronic acid, and green tea extract on facial skin results in the reduction in wrinkle numbers and depth. Clinically, an improvement in skin thickness was also observed.

Figure 3:
FIG. 3 is a photograph of an individual's hand manifesting symptoms of solar lentigo prior to the application of the disclosed composition.
Figure 4:
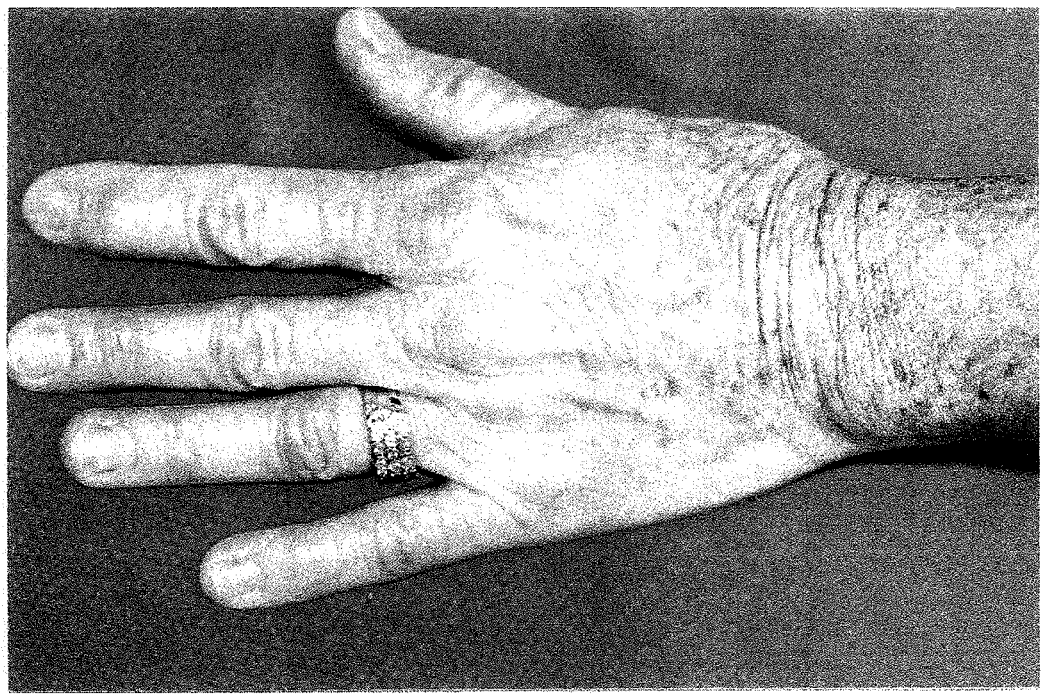
FIG. 4 is a photograph of the hand in FIG. 3 after completing the four month clinical trial described in Example 1 below.

The composition was also applied to the patients' hands. FIG. 3 is a photograph of a patient's hand at the beginning of the clinical trial. Solar lentigos, sunspots, and keratoses associated with photo-aging are evident. At the completion of the four month clinical trials, the hands of individuals reflect a marked reduction in the number of solar lentigos, an improvement in the overall color and elasticity of the skin, and reduction of keratoses as seen in FIG. 4. FIG. 4 is a photograph of the hands in FIG. 3 after four months of applying the cream comprising estriol, estradiol, hyaluronic acid, and green tea extract.

Example 2

In Vitro Percutaneous Absorption of Topical Estrogen Anti-Aging Formulations in Human Skin In vitro percutaneous absorption and skin bioavailability of radiolabeled topical estrogen skin anti-aging formulations in intact human cadaver skin versus human facelift skin were evaluated. Cumulative transdermal absorption of radiolabeled estradiol and estriol were measured at 1, 6, 12 and 24 hours. Tissue compartment (epidermis, dermis) recovery was measured at 24 hours.

The experimental design for the in vitro percutaneous studies is outlined in Table 1 below:

TABLE 1

Experimental design for skin penetration studies

| Donor Skin | Number of Samples | 1 Hr | 6 Hr | 24 Hr |
|---|---|---|---|---|
| Cadaver-female | 3-6 | 3 | 3 | 3T |
| Facelift-Face | 3-6 | 3 | 3 | 3T |
| Facelift-Neck | 3-6 | 3 | 3 | 3T |

3 (Res Sample)
T (Tissue Compartments)

Human cadaver skin was obtained from a single female donor. The skin was dermatomed to approximately 300 micron thickness. Skin was excluded if it is damaged, has irregularities (for example, scar tissue, holes, birthmarks, etc.) or was from donors with an infectious disease. Skin samples were frozen until use. Cadaver skin specimens were thawed overnight in the refrigerator in plastic sealed bags prior to the experiment. Freshly excised human skin from the face or neck was obtained from cosmetic surgery procedures. The skin was stored in gauze moistened with isotonic phosphate buffered saline and kept cold during transport. Skin specimens were stored in the moistened gauze and refrigerated until use. A representative 4 mm skin biopsy was obtained from the donor skin and processed for Hematoxylin & Eosin (H&E) staining.

Test formulations comprising 0.1 w/w % estriol, 0.02 w/w % of estradiol, 0.2 w/w % of hyaluronic acid, and 0.2 w/w % of green tea extract were spiked with radiolabeled estradiol prior to the experiment. This was accomplished by diluting the radiolabeled compound in solvent (toluene:ethanol (9:1)) to a concentration of 1 mCi/ml. The radiolabel was aliquotted to obtain approximately 50-100 µCi for each formulation and then dried under nitrogen gas. The radiolabel was then admixed with the test formulation with spatulation by geometric dilution: 150 mg of the formulation was applied to the radiolabel and spatulated, followed by 300 mg of formulation, followed by the balance of the weight to achieve a total of 1.0 gram of spiked formulation.

More particularly, in each of the skin penetration studies, 1 gram of cold formulation was spiked with radiolabeled estriol or estradiol and 12 mg of the spiked formulation was applied to each chamber. Total radioactivity (DPM) of the formulation applied to each cell was determined. Based upon the specific activity of the radioisotopic compound, the total concentration of the radiochemical compound was calculated as follows:

Estriol: 12 mg formulation applied contains: 24 micrograms cold estriol; 0.00435 micrograms radiolabeled estriol.

Estradiol: 12 mg applied contains 0.60 micrograms cold estradiol; 0.003578 micrograms radiolabeled estradiol.

The total contribution of the radiochemical compound did not significantly affect the concentration of the estriol or estradiol in the test formulation.

To assay the final specific activity of the spiked test formulation, approximately 10-30 mg of the formulation was weighed (n=3), 100 µl samples were placed in 10 ml of Ecoscint® scintillation fluor (National Diagnostics #LS275) and counted in a Beckman Model LS 3801 liquid scintillation counter with a pre-calibrated quench curve for the radiolabel.

Equipment

The in vitro percutaneous studies utilized a total of 54 Franz static diffusion glass chambers (Crown Glass Cat #FDC-100) with a magnetic stirrer mounted on a 9-position Franz diffusion cell drive console with acrylic blocks, magnetic stirrers, and stainless steel manifolds (Crown #FDCD-9-LV). The reservoir volume of each cell was pre-calibrated. The diffusion cells were filled with an isotonic buffered (pH 7.4) saline (Bio-Whittaker Cat. #16-006Y) with 0.01% sodium azide (SIGMA Cat. #S-2002), with care to avoid bubbles at the skin interface. The diffusion cells were equilibrated to a temperature of 37° C. by a circulating water pump prior to applying the skin specimens.

Application of Test Formulations to Skin:

The human skin equilibrated to 37° C. was cut to size and placed on the chamber and sealed with an O-ring. A total of 10-30 mg of the spiked formulation was applied to the skin surface using a Gilson Microman® pipette and gently rubbed into the skin using the pipette tip. The dispensing tips were retained and counted. The mean Dose Per Mass ("DPM") retained by the dispensing tips was calculated and subtracted from the theoretical DPM to determine the mean total DPM applied to each chamber. The skin surface area exposed to the test formulations was up to 1.77 $cm^2$ (15 mm diameter). Penetration chambers were available in sizes of 5 mm, 9 mm, and 15 mm diameter.

For the control group, Estrogel® (0.06% estradiol gel) was applied to skin samples to compare the percutaneous absorption of the claimed composition with a marketed product for transdermal delivery of estrogen.

Sample Collection

At 1, 6, and 24 hours, a 1.0 ml sample was removed from the reservoir using a calibrated Gilson P1000 Pipetteman® micropipette, and the volume was replaced with 1.0 ml saline solution. The samples were placed in a scintillation vial containing Ecoscint® scintillation fluor (National Diagnostics #LS-275) and equilibrated overnight in the dark before counting.

At the final time point (24 hours,), the skin surface was wiped with a wet paper towel to remove residual test formulation from the skin surface.

The skin specimens were removed from the chamber and placed dermis side down onto a flat surface. The stratum corneum was removed by tape-stripping the skin with cellophane tape until glistening (approximately 20 strips) or until epidermal separation started to occur. Following tape stripping, the dermis and epidermis were separated using microwave technique (2-5 seconds). The separated epidermis was placed in a vial containing 1 ml of Soluene 350 (Packard, Inc. #6013319) was added to the digested tissues, counted in a Beckman LSC, and corrected for quenching.

The percent of radiolabeled drug recovered in the reservoir and skin compartments (epidermis, dermis) was determined by calculating the percent of the total applied DPM recovered in the respective compartments. The results of the skin penetration study are represented graphically in FIG. 3, as will be described in greater detail below.

The total micrograms of drug recovered in each compartment was obtained by multiplying the percent recovery by the total amount (micrograms) of drug applied to each chamber.

Data Entry/Calculations

The DPM data from the LSC tapes, measurements for cell volume, and quantity of drug applied were entered into a standardized Quattro Pro spreadsheet. The data entry and computer calculations were verified to be accurate as were the tables, graphs, and calculations generated by the spreadsheet.

Data were calculated after discarding outlier values for each compartment. A value was considered to be an "outlier" if the questionable value differed from the re-calculated average by more than four times the average deviation of the remaining values (Skoog & West, Analytical Chemistry). After deleting the data for cells which had outlying reservoir values, the remaining skin compartments (epidermis, dermis) were then subjected to the criteria for outliers, and were separately deleted if they meet the criteria.

RESULTS & CONCLUSIONS

Figure 5:
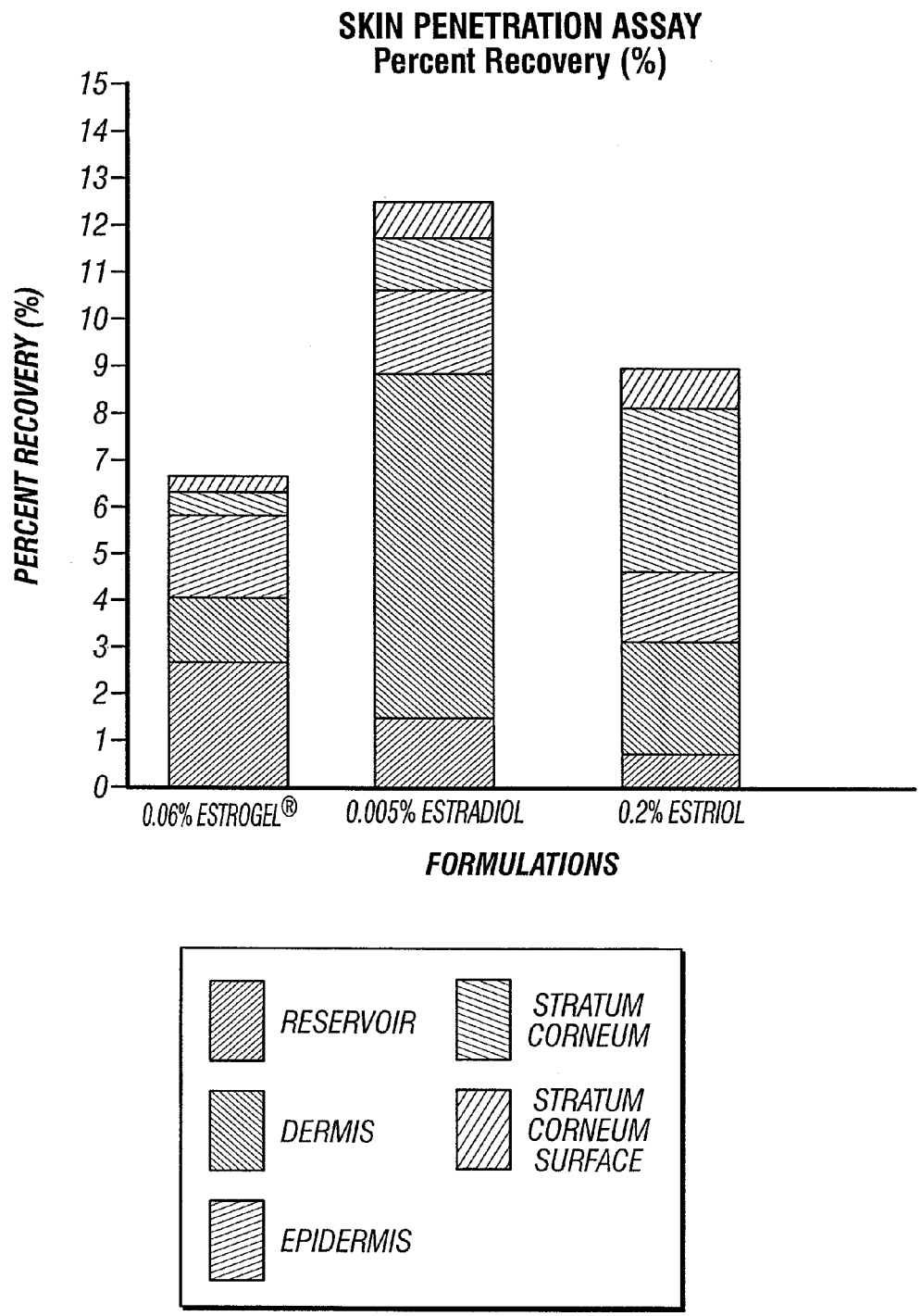
FIG. 5 is a bar graph illustrating the results of the skin penetration assay detailed in Example 2 of the specification.

Analysis of the results of the experiments revealed that estriol and estradiol penetrated the epidermis and dermis layer of the skin with minimal to no transdermal penetration. Turning to FIG. 5, FIG. 5 is a bar graph illustrating the percent recovery of radioactively labeled estradiol and estriol of the present composition as compared with a conventional estrogen-containing topical formulation, Estrogel®, in the various layers of the skin surface. The estradiol and estriol of the test formulations exhibited excellent penetration of the dermis, epidermis, stratum corneum surface, and stratum corneum. However, as evidenced by FIG. 5, the amount of systemic absorption of estradiol and estriol (reflected in the "reservoir") was significantly less than the conventional, FDA-approved topical hormonal replacement cream, Estrogel®. Moreover, the results demonstrated that the disclosed composition was more effective in transdermal and cutaneous delivery of estradiol than Estrogel®. However, as lower concentrations of estradiol were contained in the disclosed composition, the total transdermal and cutaneous delivery of estradiol was less in the composition as compared with Estrogel®. The mean transdermal delivery of estradiol was 0.07 micrograms for Estrogel® versus 0.04 micrograms for the disclosed composition. The total surface area to which the 12 mg of formulation was applied was 0.068 $cm^2$. The percent transdermal and cutaneous delivery of the estriol was approximately the same as the estradiol (Estrogel®). However, since the disclosed composition contained higher estriol concentrations, the total micrograms delivered transdermally and cutaneously was higher with estriol than with estradiol.

Example 3

Use of Estriol, Estradiol, Green Tea Extract, and Hyaluronic Acid to Treat Urge Incontinence An individual suffering from urge incontinence is identified. The individual is administered 2 grams of a vaginal cream comprising 0.2 w/w % estriol; 0.01 w/w % estradiol, 1.0 w/w % hyaluronic acid, and 0.2 w/w % green tea extract using an applicator three times a week until the urge incontinence is resolved.

After treatment, improved bladder control is observed with a reduction in incontinence.

Example 4

Use of Estriol, Estradiol, Green Tea Extract and Hyaluronic Acid to Treat Vaginal Dryness An individual presenting with vaginal dryness associated with menopause is identified. The individual is administered intravaginally a foam comprising 0.4 w/w % estriol; 0.03 w/w % estradiol, 5 w/w % hyaluronic acid, and 0.1 w/w % green tea extract once a day as needed. Following treatment, an increase in vaginal moisture is observed.

Example 5

Use of Estriol, Estradiol, Green Tea Extract, Hyaluronic Acid, Date Palm Extract, and Ascorbic Acid to Treat Signs of Skin Aging An individual presenting with wrinkles and sun damage is identified. The individual is administered topically a cream comprising 0.2 w/w % estriol, 0.01 w/w % estradiol, 0.2 w/w % hyaluronic acid, 0.2 w/w % green tea extract, 0.1 w/w % ascorbic acid, and 5.0 w/w % date palm extract twice daily. A reduction in wrinkle depth and amelioration of damage caused by the sun is observed following treatment.

Example 6

Use of Composition Comprising Estriol, Estradial, Hyaluronic Acid, and Green Tea Extract for the Treatment of Rosacea A patient presenting with rosacea was treated by administering a topical formulation comprising 0.02 w/w % estriol, 0.01 w/w % estradiol, and 0.2% hyaluronic acid professionally compounded in Dermabase Cream™ (Paddock Laboratories, Minneapolis, Minn.) as described above with reference to Example 1. The formulation also included 0.2 w/w % green tea extract. FIG. 6 includes photographs of the patient taken prior to the initiation of treatment. Notice, prior to treatment, the patient presented with confluent erythematous papules on the cheeks, chin, and forehead with an increase in capillaries, flushing, and telangiectasia. The composition was administered twice daily for a period of four months. At the conclusion of the clinical trial, a photograph was taken of the patient. See FIG. 7. A marked reduction in redness and minimization of bumps were observed on the surface of the patient's skin after treatment with the composition. A significant improvement and reduction of papules and erythema.

The foregoing description details certain embodiments of the instant disclosure. It will be appreciated, however, that no matter how detailed the foregoing appears in text, the invention can be practiced in many ways. Certain modifications to the compositions and methods described herein will be apparent to one of ordinary skill in the art. The claims appended hereto are intended to encompass these modifications. As is also stated above, it should be noted that the use of particular terminology when describing certain features or aspects of the invention should not be taken to imply that the terminology is being re-defined herein to be restricted to including any specific characteristics of the features or aspects of the disclosure with which that terminology is associated. The scope of the invention should therefore be construed in accordance with the appended claims and any equivalents thereof All references and patents cited herein are incorporated by reference.

What is claimed is:

1. A method for treating the symptoms of skin aging, comprising:
    identifying an individual presenting with symptoms of skin aging; and
    topically administering to said individual a pharmaceutically effective dose of a composition, consisting essentially of:
        a pharmaceutically effective amount of estriol;
        a pharmaceutically effective amount of estradiol;
        a pharmaceutically effective amount of hyaluronic acid;
        a pharmaceutically effective amount of green tea extract; and
        a pharmaceutically acceptable carrier; wherein said estriol comprises between about 0.01 to about 3.0 w/w %, said estradiol comprises between about 0.0001 to 3.0 w/w %, said hyaluronic acid comprises between about 0.01 to about 50.0 w/w %; and said green tea extract comprises between about 0.01 to about 10.0 w/w %.

2. The method of claim 1, wherein said pharmaceutically acceptable carrier is selected from the group consisting of a cream, an ointment, a lotion, a gel, a salve, and an aerosol spray.

3. The method of claim 1, wherein said individual is a post-menopausal female.

4. The method of claim 1, wherein said individual is a pre-menopausal female.

5. The method of claim 1, wherein said individual is a male.

6. The method of claim 1, wherein said symptoms of skin aging are selected from the group consisting of rhytids, wrinkles, jowls, sun damage, dull appearance of skin, loss of skin taughtness, keratosis, hyperpigmentation, melasma, solar lentigo, solar keratosis, dermatoheliosis, and skin discoloration.

7. A method for treating the symptoms of skin aging, comprising:
    identifying an individual presenting with symptoms of skin aging; and
    topically administering to said individual a pharmaceutically effective dose of a composition, consisting essentially of:
        a pharmaceutically effective amount of estriol;
        a pharmaceutically effective amount of estradiol;
        a pharmaceutically effective amount of hyaluronic acid;
        a pharmaceutically effective amount of green tea extract;
        a pharmaceutically effective amount of ascorbic acid, wherein said pharmaceutically effective amount of ascorbic acid is between about 0.01 to about 10.0 w/w %; and
        a pharmaceutically acceptable carrier: wherein said estriol comprises between about 0.01 to about 3.0 w/w %, said estradiol comprises between about 0.0001 to 3.0 w/w %, said hyaluronic acid comprises between about 0.01 to about 50.0 w/w %; and said green tea extract comprises between about 0.01 to about 10.0 w/w %.

8. A method for treating the symptoms of skin aging, comprising:
    identifying an individual presenting with symptoms of skin aging; and
    topically administering to said individual a pharmaceutically effective dose of a composition, consisting essentially of:
        a pharmaceutically effective amount of estriol;
        a pharmaceutically effective amount of estradiol;
        a pharmaceutically effective amount of hyaluronic acid;
        a pharmaceutically effective amount of green tea extract;
        a pharmaceutically effective amount of date palm extract, wherein said pharmaceutically effective amount of date palm extract is between about 0.01 and 25 w/w %; and
        a pharmaceutically acceptable carrier; wherein said estriol comprises between about 0.01 to about 3.0 w/w %, said estradiol comprises between about 0.0001 to 3.0 w/w %, said hyaluronic acid comprises between about 0.01 to about 50.0 w/w %; and said green tea extract comprises between about 0.01 to about 10.0 w/w %.

* * * * *